(12) United States Patent
Styrc

(10) Patent No.: US 7,806,927 B2
(45) Date of Patent: Oct. 5, 2010

(54) INTERCHANGEABLE PROSTHETIC VALVE

(75) Inventor: Mikolaj Witold Styrc, Kopstal (LU)

(73) Assignee: Laboratoires Perouse, Ivry le Temple (FR)

( * ) Notice: Subject to any disclaimer, the term of this patent is extended or adjusted under 35 U.S.C. 154(b) by 223 days.

(21) Appl. No.: 11/661,939

(22) PCT Filed: Sep. 7, 2005

(86) PCT No.: PCT/FR2005/002229

§ 371 (c)(1), (2), (4) Date: Aug. 1, 2007

(87) PCT Pub. No.: WO2006/027500

PCT Pub. Date: Mar. 16, 2006

(65) Prior Publication Data

US 2008/0039934 A1 Feb. 14, 2008

(30) Foreign Application Priority Data

Sep. 7, 2004 (FR) .................................. 04 09468

(51) Int. Cl.
*A61F 2/06* (2006.01)
(52) U.S. Cl. .................................. 623/2.11
(58) Field of Classification Search ........ 623/2.11–2.38
See application file for complete search history.

(56) References Cited

U.S. PATENT DOCUMENTS

| | | | |
|---|---|---|---|
| 6,730,118 B2 * | 5/2004 | Spenser et al. | 623/1.24 |
| 6,821,297 B2 * | 11/2004 | Snyders | 623/2.18 |
| 6,893,460 B2 * | 5/2005 | Spenser et al. | 623/2.14 |
| 7,252,682 B2 * | 8/2007 | Seguin | 623/2.17 |
| 7,267,686 B2 * | 9/2007 | DiMatteo et al. | 623/1.24 |
| 7,429,269 B2 * | 9/2008 | Schwammenthal et al. | 623/2.14 |
| 7,442,204 B2 * | 10/2008 | Schwammenthal et al. | 623/1.24 |
| 7,455,689 B2 * | 11/2008 | Johnson | 623/2.18 |
| 7,481,838 B2 * | 1/2009 | Carpentier et al. | 623/2.18 |
| 7,524,331 B2 * | 4/2009 | Birdsall | 623/2.11 |
| 2002/0032481 A1 * | 3/2002 | Gabbay | 623/2.11 |
| 2003/0040792 A1 * | 2/2003 | Gabbay | 623/2.11 |
| 2004/0019374 A1 | 1/2004 | Hojeibane et al. | |
| 2004/0098112 A1 | 5/2004 | DiMatteo et al. | |
| 2004/0193253 A1 | 9/2004 | Thorpe et al. | |
| 2007/0255400 A1 * | 11/2007 | Parravicini et al. | 623/2.41 |
| 2008/0077234 A1 * | 3/2008 | Styrc | 623/2.11 |
| 2008/0161911 A1 * | 7/2008 | Revuelta et al. | 623/2.17 |

FOREIGN PATENT DOCUMENTS

| | | |
|---|---|---|
| WO | 98/11847 | 3/1998 |
| WO | 02/087467 | 11/2002 |
| WO | 03/030776 | 4/2003 |

* cited by examiner

*Primary Examiner*—Suzette J Gherbi
(74) *Attorney, Agent, or Firm*—Wenderoth, Lind & Ponack, L.L.P.

(57) ABSTRACT

The invention relates to a prosthetic valve which is endoluminally placeable and comprises a tubular support radially deformable with respect to a main axis (X-X) from an unfolded implanting position to a folded setting position. A flexible plug connected to the tubular support and deformable between a blocking position in which it is transversally stretched and a releasing position in which it is transversally contracted by the action of a flow circulating through said tubular support. The inventive valve also comprises a rigid chord which extends generally along the generatrix of the tubular support and is connected thereto at least at two points which are remote from each other along the axis thereof.

20 Claims, 5 Drawing Sheets

INTERCHANGEABLE PROSTHETIC VALVE

BACKGROUND OF THE INVENTION

The present invention relates to a prosthetic valve to be put into place by an endoluminal approach, the valve being of the type involving a tubular support that is radially deformable relative to a main axis between a deployed implantation position and a folded positioning position; and a flexible shutter connected to the tubular support and deformable between an obstruction position in which it extends transversally and a release position in which it is contracted transversally under the action of a flow of blood through the tubular support.

The heart comprises two atriums and two ventricles which are separated by valves. Valves are also present at the outlets from the right ventricle (pulmonary valve) and from the left ventricle (aortic valve).

These valves ensure that blood flows in one direction only, avoiding reflux of blood at the end of ventricular contraction.

Valves can suffer diseases. In particular, they can suffer from poor opening, thus reducing the flow of blood, or from being somewhat leaky, thus allowing a reflux or regurgitation of blood back into the ventricle that has just expelled it.

These regurgitation problems lead to abnormal expansion of the ventricle thereby producing, in the long run, heart failure.

It is known to treat that type of disease surgically, by replacing the diseased valve. Diseased valves, and in particular the aortic valve at the outlet from the left ventricle, are replaced by valves taken from a deceased subject, or by prosthetic valves commonly referred to as bioprostheses. A prosthetic valve is constituted by a metal ring structure and a flexible shutter made of tissue of animal origin. The shutter is permanently secured to the structure.

Such valves are described in particular in documents WO 01/03095 and WO 00/27975.

Once implanted, the structure bears against the inside wall of the heart to which it is sutured, in particular at the inlet to the aortic valve coming from the left ventricle.

It is found that after such a prosthesis has been implanted for several years, it degenerates and no longer functions efficiently. In particular, the flexible shutter tears and develops holes, or the shutter becomes calcified and thus loses flexibility, thus no longer being capable of deforming to perform its valve function. It is then necessary to put a new prosthesis into place.

However, it is not possible to remove the old prosthesis via an endoluminal path, in particular because the carrier structure of the prosthesis is sutured to the wall of the heart, meaning that they cannot be separated without major surgery for complete replacement of the valve.

In order to avoid a major surgical operation for removing the old prosthesis and putting a second prosthesis into place, it has been proposed that a new prosthetic valve could be put into place by an endoluminal approach inside the old prosthesis which is left in place.

The new prosthetic valve is formed by a tubular support constituted by a radially deformable lattice fitted with a flexible shutter disposed in the duct defined by the tubular support. The shutter is connected to the tubular support and presents a shape that enables it, by deforming, to allow blood to flow in one direction and to prevent from flowing in the opposite direction.

It has been proposed that the tubular support could be made of interlaced resilient metal wires defining meshes that are generally lozenge-shaped. Such a tubular support is known as a "stent". The tubular support is deformable between an insertion position, in which its diameter is reduced, and an implantation position in which its diameter is larger and sufficient to enable the support to bear against the inside of the carrier structure of the old prosthesis.

In order to be put into place, such prosthetic valves comprising a tubular lattice support are disposed inside a small-diameter catheter. The end of the catheter is brought via the arterial network to the region where the no longer functioning, old prosthesis has been fitted. The new prosthetic valve is pushed out from the catheter using a wire-shaped member engaged in the catheter. Since the tubular support is resilient, it deploys immediately on its own when it is no longer compressed radially by the catheter. It then comes to bear around the inside perimeter of the carrier structure of the old prosthesis.

The new prosthetic valve is then put into place while the heart is still beating. When treating an aortic valve, the prosthetic valve is brought in against the flow of blood. Thus, while the new prosthetic valve is being deployed, it deploys at the inlet to the aortic artery, thereby obstructing it. During deployment, the new prosthetic valve presents a transverse surface area that is large. Thus, during a contraction of the heart leading to blood being expelled into the aorta, the prosthetic valve runs the risk of being entrained during deployment, and can thus end up being positioned away from the carrier structure of the old valve. The new valve then obstructs the artery without performing its function in a satisfactory manner.

The consequences of the new prosthetic valve being wrongly positioned are often very damaging for the patient, since the newly-inserted prosthetic valve cannot be withdrawn other than surgically.

In order to avoid that difficulty, it is known to deploy the new prosthetic valve quickly and exactly between two contractions of the heart. However, since that length of time is very short, it is difficult to put the new prosthetic valve into place.

SUMMARY OF THE INVENTION

An object of the invention is to propose a prosthetic valve that can be put into place by an endoluminal approach without major risk of the valve being wrongly positioned axially, even in the presence of a powerful flow of blood in the region where it is being implanted.

To this end, the invention provides an interchangeable prosthetic valve of the above-specified type, characterized in that it comprises at least one rigid member extending generally along a generator line (and along an axial direction) of the tubular support.

The member is connected to the tubular support at least two points that are spaced along the axis of the tubular support.

In particular embodiments, the prosthetic valve includes one or more of the following characteristics:
 the tubular support defines a solid cylindrical wall that is liquid-proof;
 the tubular support comprises a tubular lattice covered in a stretchable film that is liquid-proof and that forms the solid cylindrical wall;
 each member is engaged in alternation in the meshes of the lattice;
 the tubular support presents a generally cylindrical middle trunk and, axially at each end of the trunk, two generally frustoconical collars flaring away from the trunk towards the ends of the supports;

the tubular support is resilient and is shaped to be urged resiliently from its folded position towards its deployed position;

each member has a projecting end for connection to a prop for holding the prosthetic valve in place;

the tubular support is extended by converging legs forming a tripod, which legs are connected to one another at a connection point lying substantially on the axis of the tubular support; and the shutter has three membranes that are deformable between a closed position in which the free edges of the membranes touch one another in pairs over half their length, and an open position for passing the flow of blood in which the three membranes are spaced apart from one another.

The invention also provides a treatment kit comprising:

a prosthetic valve as described above;

a catheter for putting the valve into place; and a prop for holding the prosthetic valve. The prop includes means for interconnecting it in line with the member of the prosthetic valve.

BRIEF DESCRIPTION OF THE DRAWINGS

The invention can be better understood upon reading the following description given purely by way of example and made with reference to the drawings, in which.

DETAILED DESCRIPTION OF THE INVENTION

Figure 1:
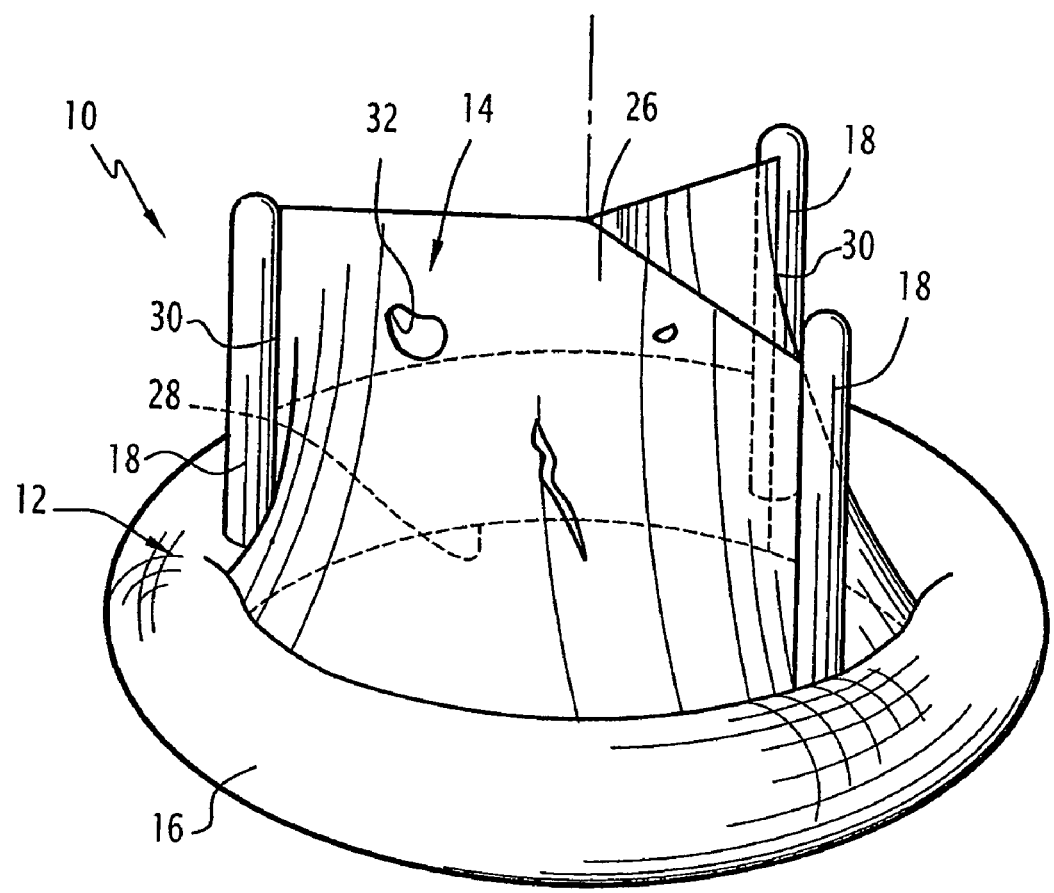
FIG. 1 is a perspective view of a surgically-implanted prosthetic valve that is damaged.

FIG. 1 shows a prosthetic valve 10 that is damaged and needs to be treated. The prosthetic valve is assumed to have been implanted surgically, e.g. to replace an aortic valve of the heart. Thus, this valve is placed immediately upstream from the aorta at the location of the natural valve.

Such a prosthetic valve is known per se, and essentially comprises a carrier structure 12 and a flexible shutter 14.

The carrier structure 12 essentially comprises a rigid ring 16 carrying three rigid pegs 18 each extending parallel to the axis of the ring 16. The ring is constituted by a rigid metal torus to which the three pegs 18 are welded. The torus is covered over its entire surface in a woven sheet enabling the prosthetic valve to become secured to heart tissue by suturing between the woven sheet and the wall of the heart. The inside diameter of the ring 16 lies in the range 15 millimeters (mm) to 40 mm.

Each peg 18 is connected at one end to the ring 16 and all of the pegs project from the same side thereof. The pegs are regularly distributed angularly around the axis of the carrier structure 12. The total height of the pegs 18, including the ring 16, lies in the range 10 mm to 30 mm.

The flexible shutter 14 is permanently secured simultaneously to the pegs 18 and to the ring 16. In the embodiment shown, the flexible shutter is made up of three membranes 26 of generally rectangular shape. Along a base-forming long side 28, each membrane 26 is connected to the carrier structure between two successive (adjacent) studs 18. Thus, along the base, the membrane describes a circular arc along the ring 16. The two side edges of the membrane are connected lengthwise along the pegs 18.

In a known manner, the three membranes 26 forming the flexible shutter are normally deformable between a closed position in which the three edges of the membranes touch one another, the membranes externally defining three pouches for accumulating blood by being deformed towards the axis of the prosthetic valve, and an open position in which the three membranes are spaced apart from one another, extending generally axially from the ring, the three membranes then together defining a generally cylindrical passage allowing the blood stream to flow.

As shown in FIG. 1, the prosthetic valve 10 is damaged by holes 32 formed in the membranes 26, these holes causing the valve to seal poorly.

Figure 2:
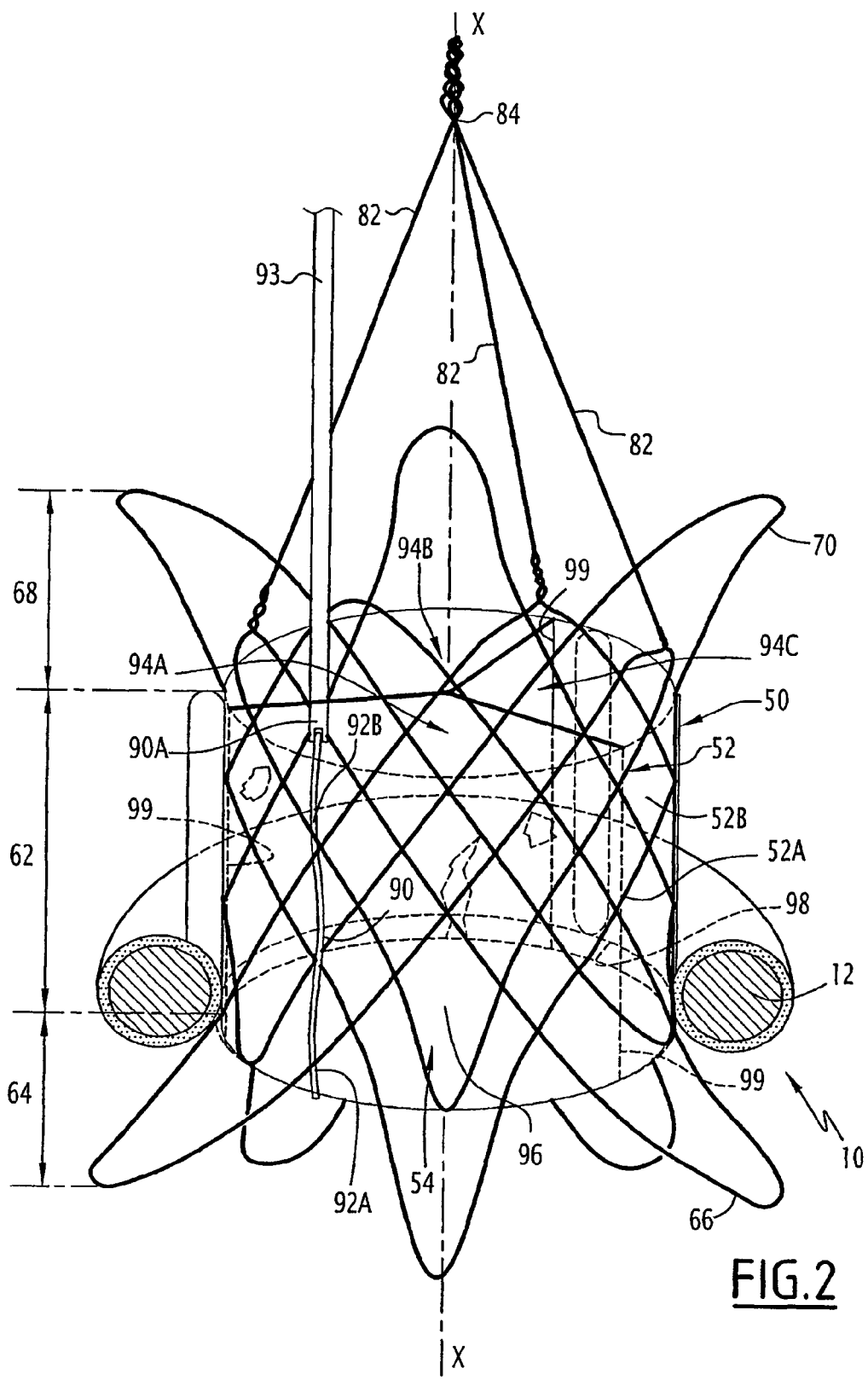
FIG. 2 is a perspective view of a prosthetic valve of the invention in its closed state, the valve being in the process of being implanted through an old prosthetic valve that is damaged.

FIG. 2 shows a prosthetic valve 50 of the invention put into place by an endoluminal approach inside the damaged prosthetic valve 10 that has previously been implanted surgically.

The prosthetic valve 50 comprises a lattice tubular support 52 of axis X-X and a flexible shutter 54 connected to the tubular support 52 and placed inside it.

The valve 50 is replaceable and is normally removable relative to the damaged valve 10.

The tubular support 52 is constituted, for example, by a tubular lattice 52A embedded in a stretchable film 52B that is liquid-proof, such as an elastomer. Since the film 52B covers the lattice, it defines, over the entire height of the support 52, a cylindrical wall that is solid and liquid-proof. The lattice 52A is made of stainless steel having elastic properties, such that the support 52 is self-expanding. Such a support, when used on its own, is commonly referred to as a "stent".

As is known, the support 52 can deform spontaneously from a compressed state in which it has a small diameter to a dilated (expanded) state in which it has a diameter that is greater, the dilated (expanded) state constituting its rest state.

Figure 3:
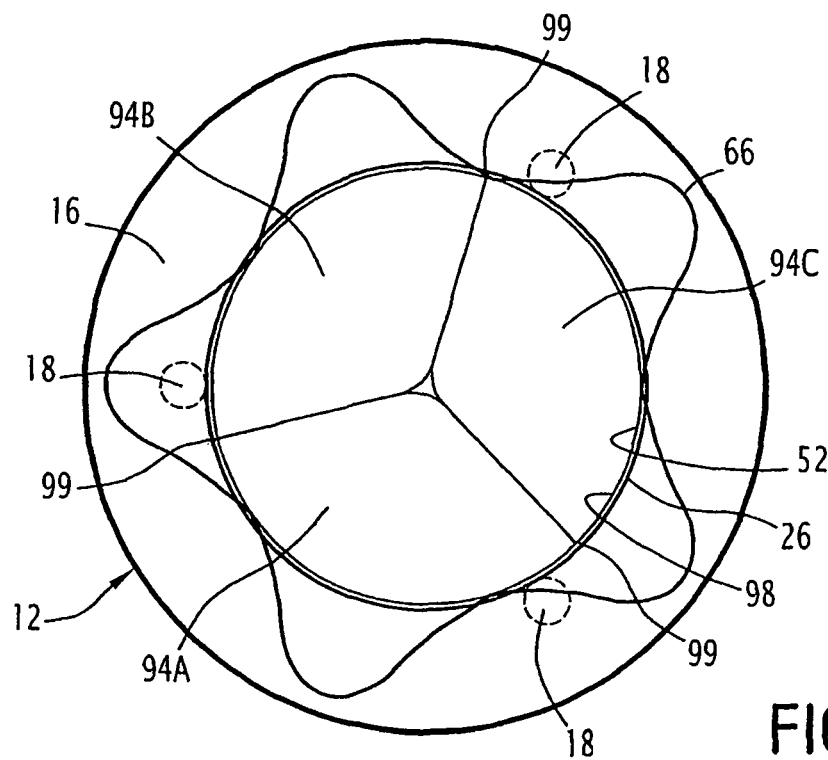
FIG. 3 is an end view of the FIG. 2 prosthetic valve.
Figure 4:
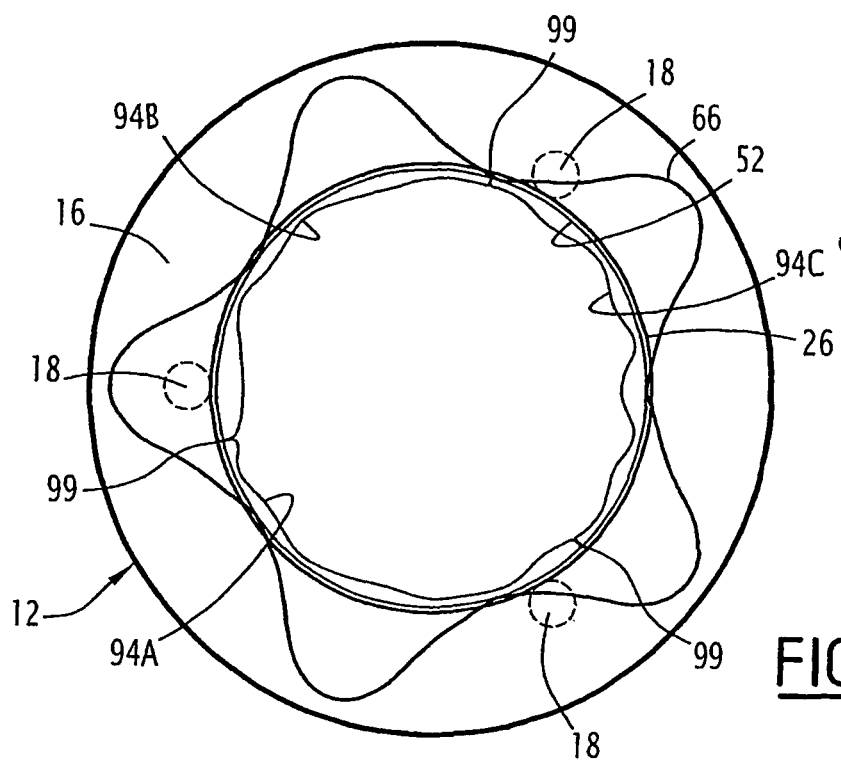
FIG. 4 is a view identical to that of FIG. 3, the prosthetic valve being in its open state.

In its implanted state as shown in FIGS. 2 to 4, and because of its resilience, the support 52 bears against the ring 16 and the pegs 18 of the damaged valve 10, holding the three membranes 26 pressed against the outside surface of the support 52.

At each of its axial ends, the support 52 extends axially beyond the carrier structure of the damaged valve 10 by two diverging collars that are generally truncated in shape, flaring towards the axial ends of the support.

More precisely, the support 52 presents a middle trunk 62 that is generally cylindrical, having a length corresponding to the height of the carrier structure of the damaged valve, this height being measured along the axis of the valve. The height of the trunk lies in the range 10 mm to 30 mm.

The lattice defining the trunk 62 is made up of interlaced metal wires. Thus, two families of wires cross over one another. The wires in the first family define helixes oriented in the same direction and extending generally parallel to one another. The wires of the second family define helixes oriented in the opposite direction and extending parallel to one another. The wires of the first and second families are engaged successively over and under one another, such that these families of wires define lozenge-shaped meshes, with one diagonal of each mesh extending along the axis of the support, and with its other diagonal extending generally perpendicularly.

At a first end of the support, the trunk 62 is extended by a first flared collar 64 constituted by a set of lobes 66 going away from the axis of the support towards their curved ends. These lobes are formed by loops made at the ends of the wires of the first and second families, and they are integral therewith.

Similarly, at its second end, the support has a second flared collar 68 extending the trunk 62. This collar is likewise defined by outwardly-deformed lobes 70.

At rest, the free ends of the collars, i.e. the most highly-flared end sections of the collars, define an outline of diameter equal to the diameter of the trunk 62 plus 5 mm to 15 mm.

Similarly, and advantageously, the height of the collars 64, 68, measured along the axis of the tubular support 52 lies in the range 5 mm to 15 mm, and for example is equal to 10 mm.

The film 52B in which the tubular lattice 52A is embedded extends over the lobes forming the collars 64 and 68.

In a first embodiment, the tubular support 52 has over its entire height while at rest, i.e. when it is not compressed in a structure 12, a diameter that is greater than the diameter of the structure 12. Thus, the collars 64 and 68 take up a flared shape merely because of the natural resilience of the tubular support while the trunk is kept confined in tubular shape within the carrier structure 12 of the damaged prosthetic valve.

In a variant, the trunk 62 of the tubular support when at rest, and even when not compressed inside a structure 12, has a diameter that is smaller than the end diameter of the collars 64 and 68.

Furthermore, three pairs of wires coming from the first and second families respectively are connected together in pairs at the second collar 68 to form three legs 82. The legs converge towards one another along the axis X-X of the prosthetic valve in order to meet at a connection point 84 located on the axis. The three legs 82 thus define a tripod. They are regularly distributed angularly around the axis X-X, and each of them defines relative to the axis an angle that lies in the range 20° to 40°. For connection purposes, the three legs 82 are, for example, twisted together at the point 84. A connection loop is made at the end point 84.

In addition, and according to the invention, the tubular support 52 includes at least one rigid stiffener member 90 extending generally along a generator line of the tubular support 52 (along an axial direction of the tubular support 52, as illustrated in FIG. 2). This stiffener member is connected to the support at least at two points 92A, 92B that are spaced apart along the axis of the support. These two points are formed along the height of the trunk 62, in particular in the vicinity of the regions where it connects with the collars 64 and 68. Connection may be performed by welding or by adhesive bonding.

Advantageously, a single member 90 is formed along one generator line of the trunk 62. By way of example, this stiffener member 90 is constituted by a longitudinally rigid metal wire that is engaged through the meshes of the lattice, passing alternately inside and outside the lattice.

Advantageously, the ends of the stiffener member 90 are disposed inside the tubular support, i.e. beside the axis X-X relative to the liquid-proof film 52B.

Figure 5:
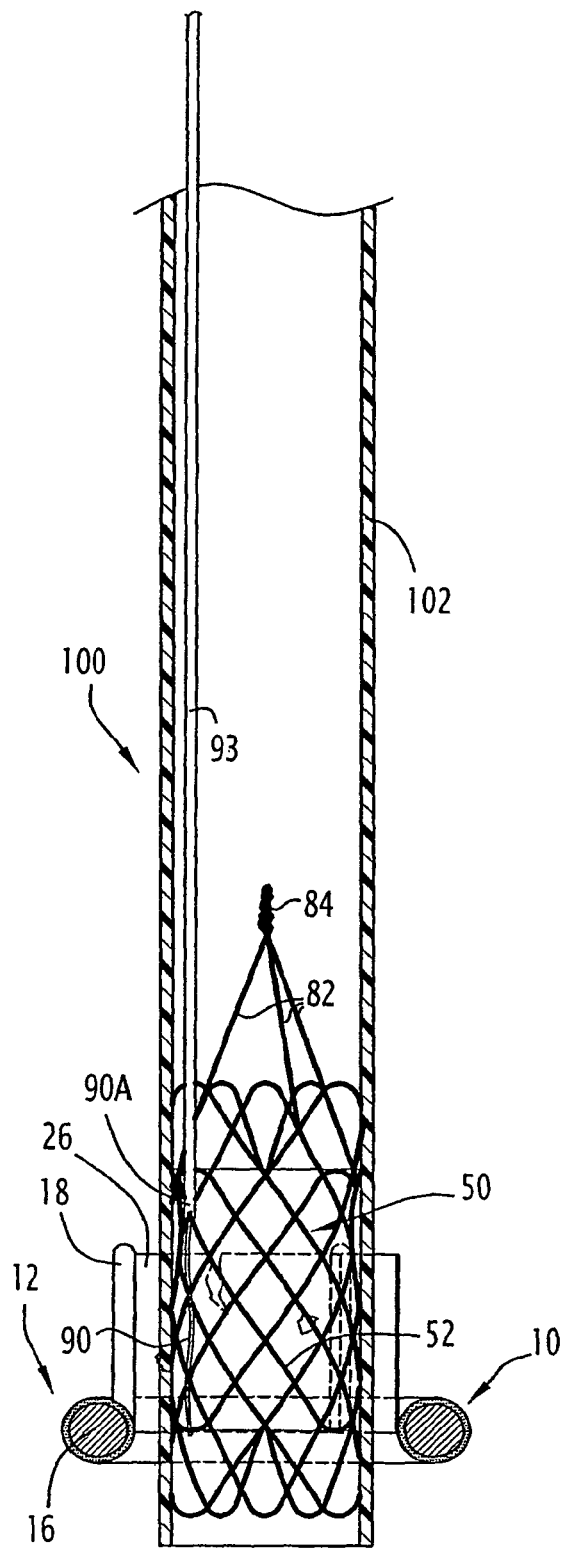
FIGS. 5 and 6 are longitudinal section views showing the successive stages of putting a prosthetic valve of the invention into place.

At least one projecting end 90A of the stiffener member 90, and in particular its second end adjacent to the legs 82, is suitable for cooperating with a prop 93 for axial connection therewith, as shown in FIG. 5 and as explained below. The axial connection between the prop 93 and the stiffener member 90 is provided, by way of example, by the connection end 90A of the member being engaged in a housing provided in the thickness of the prop 93 and opening out in the end thereof.

The shutter 54 is connected to the inside surface of the tubular support 52. This shutter is made up of three flexible membranes 94A, 94B, and 94C arranged like the shutter 14 of the prosthetic valve 10. Thus, each membrane 94A, 94B, and 94C is constituted by a polymer film or a layer of organic film such as calf pericardium. Each membrane is generally rectangular in shape. It is connected to the inside surface of the liquid-proof film 52B along a base-forming long side 98 around the connection circumference between the trunk 62 and the enlarged collar 64.

The longitudinal edges 99 of the three membranes 94A, 94B, and 94C are connected to the tubular support 52 along three generator lines thereof that are regularly distributed angularly around the axis of the tubular support. Thus, the membranes are connected in pairs along their longitudinal edges to the tubular support. This connection is performed over the entire height of the trunk 62.

The shutter-forming membranes 94A, 94B, and 94C are deformable between a closed position shown in FIGS. 2 and 3, in which the free edges of the membranes touch one another in pairs along half of their length, and a position for passing blood, as shown in FIG. 4 in which the three membranes are moved apart from one another.

In the closed position, the three membranes cooperate with the tubular wall of the support 52 to define three pouches for retaining the stream of blood. In the open position, the three membranes are pressed against the inside surface of the tubular support, as shown in FIG. 4, thus together defining a generally circular duct in which the stream of blood can flow.

Figure 6:
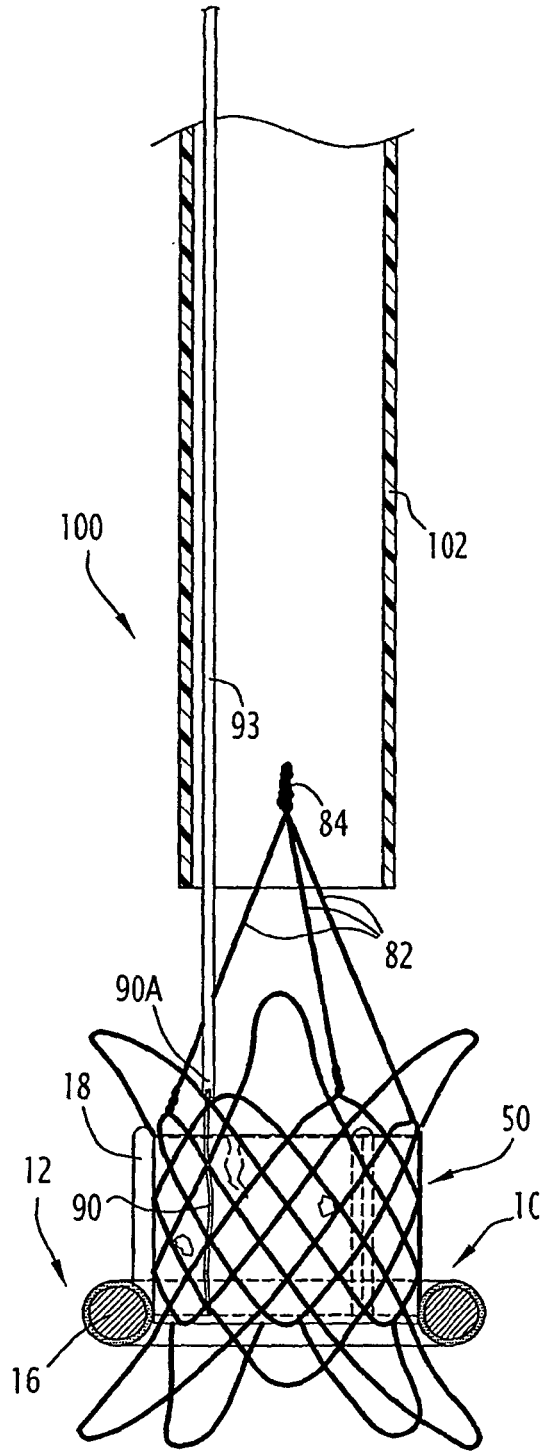

In order to treat the damaged prosthetic valve, the new prosthetic valve is put into place in the space defined by the carrier structure 12 of the damaged valve, as shown in FIGS. 5 and 6.

For this purpose, a treatment kit 100 shown in these figures is used. It comprises a new prosthetic valve 50 contained in a catheter 102 of outside diameter that is smaller than the inside diameter of the carrier structure 12.

As shown in FIG. 5, the prosthetic valve, and in particular the tubular support 52, is compressed radially inside the tube in a folded insertion position.

In addition, the prop 93 extends lengthwise along the catheter 102 being connected at its end to the end of the axial stiffener member 90. The prop 93 presents sufficient axial stiffness to be capable of pushing the prosthetic valve out from the catheter 102.

During installation of the valve, the end of the catheter 102 in which the prosthetic valve is received is inserted in the patient's aorta, and is then moved progressively along the aorta to the location of the damaged prosthetic valve at the outlet from the heart. The catheter is moved against the normal flow of blood.

The catheter is brought into the position shown in FIG. 5. In this position, the catheter 102 is then pulled while the new prosthetic valve 50 is held in place by the prop 93. As the catheter 102 moves, the prosthetic valve 50 becomes uncovered, such that its first end deploys to form the collar 64 and then the tubular support trunk 62 comes to bear against the pegs 18, and finally the second end deploys to form the collar 68.

During the progressive baring of the prosthetic valve 50 by moving the catheter 102, the prosthetic valve is held stationary in an axial direction relative to the ducts of the aorta, and in particular relative to the old prosthetic valve 10 that is damaged, by means of the rigid prop 93 which holds the stiffener member 90 in line therewith. Thus, the presence of the prop 93 cooperating with the stiffener member 90 reduces the risk of the prosthetic valve moving axially as it is being deployed, even if it is deployed during a heartbeat causing blood to flow through the location of the valve.

After deployment, the valve is held axially by the presence of the enlarged collars 64 and 68 bearing respectively on the ring 16 and on the ends of the pegs 18.

After deployment, the prop 93 is withdrawn merely by traction. Thus, the member 90 disengages from the end of the prop 93. The member 90 remains in position since it is integrated in the tubular support 52.

Figure 7:
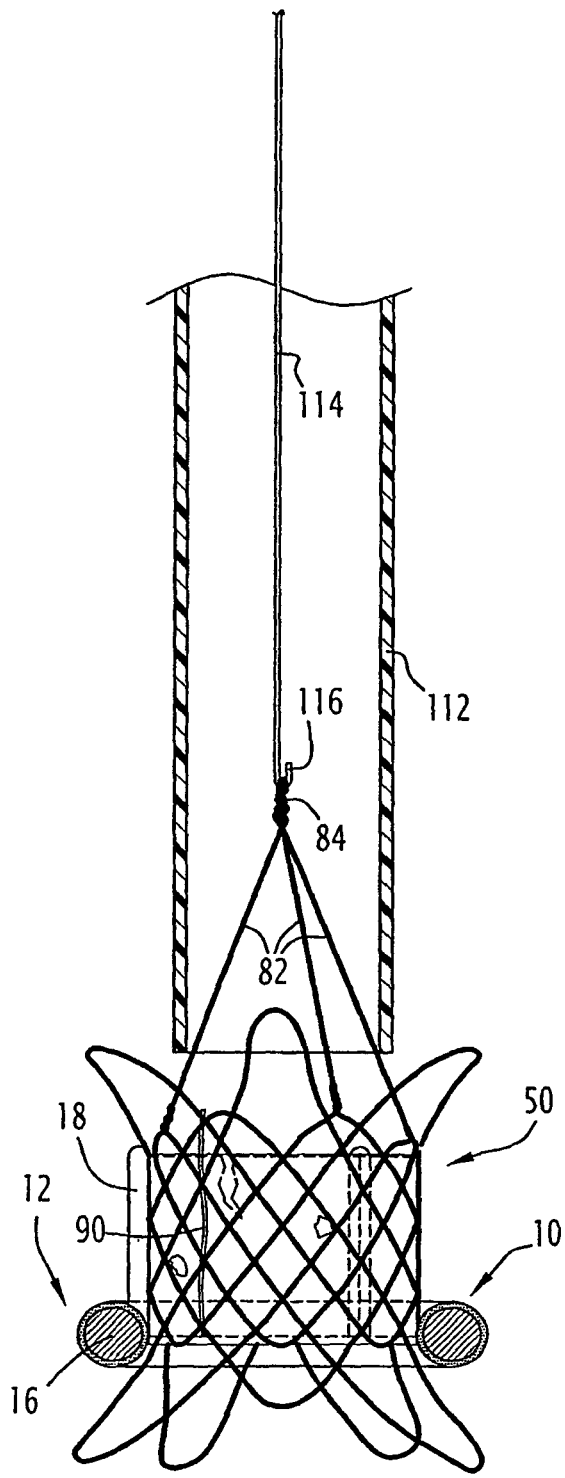
FIGS. 7 and 8 are views identical to those of FIGS. 5 and 6, showing the successive stages of removing a prosthetic valve of the invention.
Figure 8:
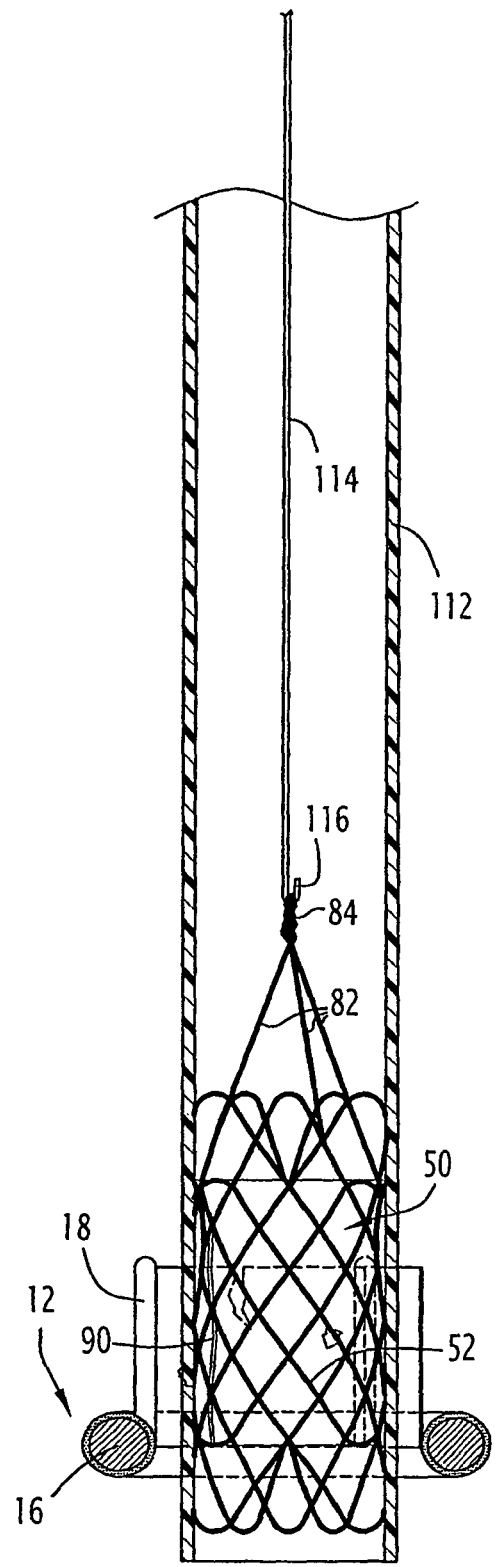

As shown in FIGS. 7 and 8, in order to withdraw the prosthetic valve 50, a catheter 112 is introduced through the aorta and is placed facing the end of the valve that presents the tripod made up of the legs 82.

A traction tool 114 is conveyed along the catheter 112. At its end, the tool has a hook 116 suitable for catching the connection point 84 of the tripod. While the open end of the catheter is in contact with the legs 82 of the tripod, the prosthetic valve 50 is progressively introduced into the inside of the catheter 112 by advancing the catheter 112 along the length of the valve 50. By a camming effect, the legs 82 are pushed towards the axis and the prosthetic valve is progressively moved into its tight state and becomes inserted in the catheter 112, as shown in FIG. 8. The catheter 112 containing the prosthetic valve 50 is then extracted from the human body.

A new prosthetic valve 50 is then introduced using a kit 100 for performing treatment in the human body, and the new valve is deployed as explained above.

The invention claimed is:

1. A prosthetic valve to be positioned by an endoluminal approach, said prosthetic valve comprising:
   a tubular support radially deformable relative to a main axis between a deployed implantation position and a folded insertion position, said tubular support comprising a liquid-proof, solid cylindrical wall, said cylindrical wall comprising a tubular lattice covered in a liquid-proof stretchable film;
   a flexible shutter connected to said tubular support and deformable between an obstruction position, wherein said shutter extends transversally, and a release position, wherein said shutter is contracted transversally under force of a flow of blood through said tubular support; and
   a rigid stiffener member extending along an axial direction of said tubular support, said stiffener member being connected to said tubular support at least at two points spaced apart along the axial direction of said tubular support, said stiffener member being alternately engaged in mesh of said tubular lattice.

2. A prosthetic valve to be positioned by an endoluminal approach, said prosthetic valve comprising:
   a tubular support radially deformable relative to a main axis between a deployed implantation position and a folded insertion position;
   a flexible shutter connected to said tubular support and deformable between an obstruction position, wherein said shutter extends transversally, and a release position, wherein said shutter is contracted transversally under force of a flow of blood through said tubular support; and
   a rigid stiffener member extending along an axial direction of said tubular support, said stiffener member being connected to said tubular support at least at two points spaced apart along the axial direction of said tubular support;
   wherein said tubular support has a cylindrical middle trunk section and a frustoconical collar at each axial end of said trunk section, each frustoconical collar flaring away from said trunk section towards a respective end of said tubular support.

3. The prosthetic valve according to claim 1, wherein said tubular support is resilient and is configured to be urged resiliently from the folded insertion position towards the deployed implantation position.

4. A prosthetic valve to be positioned by an endoluminal approach, said prosthetic valve comprising:
   a tubular support radially deformable relative to a main axis between a deployed implantation position and a folded insertion position;
   a flexible shutter connected to said tubular support and deformable between an obstruction position, wherein said shutter extends transversally, and a release position, wherein said shutter is contracted transversally under force of a flow of blood through said tubular support; and
   a rigid stiffener member extending along an axial direction of said tubular support, said stiffener member being connected to said tubular support at least at two points spaced apart along the axial direction of said tubular support,
   wherein said stiffener member has a projecting end for connection to a prop for positioning and holding said prosthetic valve in place.

5. A prosthetic valve to be positioned by an endoluminal approach, said prosthetic valve comprising:
   a tubular support radially deformable relative to a main axis between a deployed implantation position and a folded insertion position;
   a flexible shutter connected to said tubular support and deformable between an obstruction position, wherein said shutter extends transversally, and a release position, wherein said shutter is contracted transversally under force of a flow of blood through said tubular support;
   a rigid stiffener member extending along an axial direction of said tubular support, said stiffener member being connected to said tubular support at least at two points spaced apart along the axial direction of said tubular support; and
   converging legs extending from said tubular support to form a tripod, said legs being connected to one another at a connection point lying substantially on a central longitudinal axis of said tubular support.

6. A prosthetic valve to be positioned by an endoluminal approach, said prosthetic valve comprising:
   a tubular support radially deformable relative to a main axis between a deployed implantation position and a folded insertion position;
   a flexible shutter connected to said tubular support and deformable between an obstruction position, wherein said shutter extends transversally, and a release position, wherein said shutter is contracted transversally under force of a flow of blood through said tubular support; and
   a rigid stiffener member extending along an axial direction of said tubular support, said stiffener member being connected to said tubular support at least at two points spaced apart along the axial direction of said tubular support;
   wherein said shutter has three membranes deformable between a closed position, wherein free edges of said membranes touch one another in pairs over half a length of said membranes, and an open position, wherein said membranes are spaced apart from one another for allowing passage of the flow of blood.

7. The prosthetic valve according to claim 1, wherein a connection between said stiffener member and said tubular support comprises one of a weld and an adhesive bond.

8. The prosthetic valve according to claim 1, wherein said stiffener member extends along a generator line of said tubular support.

9. The prosthetic valve according to claim 1, wherein said stiffener member comprises a longitudinally rigid stiffener member extending along an axial direction of said tubular support.

10. The prosthetic valve according to claim 1, wherein said tubular support has a cylindrical trunk section, said stiffener member being mounted to said trunk section and extending along an axial direction of said trunk section.

11. A treatment kit comprising:
   a prosthetic valve to be positioned by an endoluminal approach, said prosthetic valve including:
      a tubular support radially deformable relative to a main axis between a deployed implantation position and a folded insertion position;
      a flexible shutter connected to said tubular support and deformable between an obstruction position, wherein said shutter extends transversally, and a release position, wherein said shutter is contracted transversally under force of a flow of blood through said tubular support; and
      a rigid stiffener member extending along an axial direction of said tubular support, said stiffener member being connected to said tubular support at least two points spaced apart along the axial direction of said tubular support;
   a catheter for positioning said prosthetic valve; and
   a prop for holding and positioning said prosthetic valve, said prop being configured to engage said stiffener member of said prosthetic valve, said prop extending lengthwise through said catheter such that a distal end of said prop protrudes from a distal end of said catheter during retraction of said catheter.

12. The treatment kit according to claim 11, wherein said tubular support comprises a liquid-proof, solid cylindrical wall.

13. The treatment kit according to claim 12, wherein said cylindrical wall comprises a tubular lattice covered in a liquid-proof stretchable film.

14. The treatment kit according to claim 11, wherein said prosthetic valve further includes converging legs extending from said tubular support to form a tripod, said legs being connected to one another at a connection point lying substantially on a central longitudinal axis of said tubular support.

15. The treatment kit according to claim 11, wherein said stiffener member extends along a generator line of said tubular support.

16. The treatment kit according to claim 11, wherein said stiffener member comprises a longitudinally rigid stiffener member extending along an axial direction of said tubular support.

17. The treatment kit according to claim 11, wherein said tubular support has a cylindrical trunk section, said stiffener member being mounted to said trunk section and extending along an axial direction of said trunk section.

18. The treatment kit according to claim 11, wherein said prop is further configured to disengage from said stiffener member by traction.

19. A method of treating a damaged prosthetic valve including a carrier structure and a flexible shutter, said method comprising:
   providing the treatment kit of claim 11;
   connecting the distal end of the prop to a proximal end of the stiffener member;
   inserting the prosthetic valve into the catheter;
   inserting the catheter into a blood circulation duct at a location of the damaged prosthetic valve;
   pulling the catheter out of the duct while the distal end of the prop is connected to the proximal end of the stiffener member so that the prosthetic valve is held in position by the prop, said pulling the catheter being performed so as to progressively uncover the prosthetic valve until the prosthetic valve is completely removed from the catheter and totally deployed in the damaged prosthetic valve; and
   after the prosthetic valve is totally deployed in the damaged prosthetic valve, withdrawing the prop by traction.

20. The method of claim 19, wherein the carrier structure of the damaged prosthetic valve includes a rigid ring carrying three rigid pegs, each of the pegs extending parallel to the axis of the ring, the flexible shutter being permanently secured to the pegs and to the ring, wherein said inserting the catheter into the blood circulation duct and said pulling the catheter out of the duct comprises locating the prosthetic valve so that a trunk of the tubular support bears against the pegs during deployment.

* * * * *